United States Patent [19]  [11]  4,267,355
Scott et al.  [45]  May 12, 1981

[54] PRODUCTION OF HERBICIDALLY-ACTIVE DERIVATIVES OF ALANINE

[75] Inventors: Richard M. Scott, Sittingbourne; Geoffrey D. Armitage, Whitstable, both of England

[73] Assignee: Shell Oil Company, Houston, Tex.

[21] Appl. No.: 737,313

[22] Filed: Nov. 1, 1976

[30] Foreign Application Priority Data

Nov. 5, 1975 [GB] United Kingdom ............... 45914/75

[51] Int. Cl.$^3$ .......................................... C07C 101/08
[52] U.S. Cl. .................... 560/43; 562/456; 260/501.1; 71/111; 71/115
[58] Field of Search .......... 260/471 A, 518 A, 518 R, 260/501.1, 585 R; 560/43; 71/111, 115; 562/456

[56] References Cited

U.S. PATENT DOCUMENTS 3,598,859  8/1971  Yates et al. ........................ 260/471

OTHER PUBLICATIONS

Merck Index, "Organic Name Reactions", 9th Edition, Merck and Co., N.Y. 1976.
Wagner, R. and H. Zook, "Synthetic Organic Chemistry", 1953, p. 667.
Sekeva, V. and C. S. Marvel, "Higher Alkyl Sulfonates", Journal of the American Chemical Society, vol. 55, pp. 345–346, 1933.

Primary Examiner—Donald G. Daus
Assistant Examiner—D. B. Springer

[57] ABSTRACT

Stereospecific synthesis of

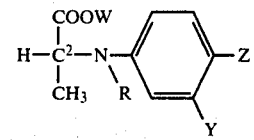

(R-configuration at $C^2$) by reaction of

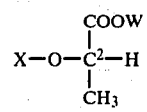

(S-configuration at $C^2$) with

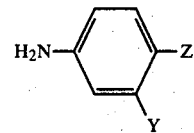

at elevated temperature in the presence of a base, e.g., R-(−)-(2-(N-benzoyl-3-chloro-4-fluoroanilino)propionic acid isopropylester) from S-(−)-isopropyl lactate mesylate and 3-chloro-4-fluoroaniline followed by benzoylation. The compounds are very active herbicides against broad-leafed weeds (R=H) or wild oats (R=(thio)benzoyl).

4 Claims, No Drawings

PRODUCTION OF HERBICIDALLY-ACTIVE DERIVATIVES OF ALANINE

This invention relates to a process for the production of herbicidally-active compounds and to compositions containing them.

It is known, for example from British Pat. Nos. 1,164,160 and 1,289,283 that certain alanine derivatives have a herbicidal action upon wild oats and, furthermore, that these compounds may be used selectively in cereal crops to control wild oats growing alongside the cereal crops. The Applicant has recently shown that certain other closely related alanine derivatives also have selective herbicidal activity in cereal crops, especially to broad-leafed weeds.

The Applicant has found that one of the optically-active isomers of these alanine derivatives is very much more active against weeds than the other isomer, and hitherto the only synthetic route available was by means of a resolution procedure. The Applicant has now found a stereospecific route which avoids the need to employ lengthy resolution techniques.

Accordingly, the present invention provides a process for the preparation of an alanine compound having the following general formula and possessing the R-configuration at carbon atom 2:

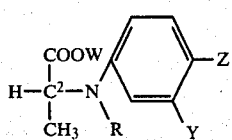

(I)

wherein Y and Z are each individually hydrogen, chlorine or fluorine;

W is hydrogen, alkyl, haloalkyl, alkenyl, cycloalkyl, aryl, alkaryl, aralkyl or a group of formula $-N=CR_1R_2$, in which $R_1$ and $R_2$ are each individually hydrogen, alkyl, aryl, aralkyl, alkaryl, alkenyl or together they form an alkylene bridge which is optionally interrupted with one or more hetero atoms, and R is hydrogen or a benzoyl or thiobenzoyl group, which comprises reacting a derivative of lactic acid of formula II possessing the S-configuration at carbon atom 2:

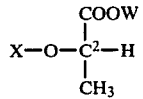

(II)

with an aniline of formula III:

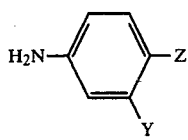

(III)

(wherein the group X—O— is a group which will leave the molecule and be replaced by a deprotonated aniline of formula III, and Z and Y have the meaning hereinbefore specified) in the presence of a base and under conditions of elevated temperature to produce a desired compound of formula I, wherein R is hydrogen, and optionally converting the last-mentioned compound into the N-benzoyl or N-thiobenzoyl derivative.

The leaving group X—O— in formula II must, as stated above, be capable of being replaced by a deprotonated aniline of formula III and suitable examples of such groups are the following: $-O.SO_2.Q$, $-O.CO.Q$ and $-O.CH(OH).CV_3$, wherein Q is a hydrocarbyl group, suitably an alkyl or aryl group containing up to 10 carbon atoms, and V is a halogen atom, e.g., chlorine, fluorine or bromine. Preferably, the leaving group X—O— is an $-O.SO_2.Q$ group, e.g., methanesulphonyl or para-toluenesulphonyl. It has been found that the presence of one of these leaving groups in the lactic acid derivative II enables the desired optically-active isomer of formula I to be obtained during the reaction of II with the aniline III. Not only is the desired optically-active isomer produced by this process but the yields are in excess of 70% and often as high as 80% or more.

Reaction between the lactic acid derivative II and the aniline III may be carried out at temperatures between 50° C. and 200° C., preferably between 130° C. and 170° C.

As with all stereospecific routes the reaction conditions must be carefully selected and tested for each particular case to ensure that the optical integrity of the required product is unaffected by these conditions. One such condition is the nature of the base present in the reaction between the lactic acid derivative II and the aniline III; the base may be organic or inorganic, preference being given to the use of alkali metal carbonates or bicarbonates. Especially good results have been obtained with sodium carbonate. Alternatively, the amine III itself may be used as the base if desired.

The aniline III may be employed as the solvent for the reaction but an additional solvent may be employed if this assists reaction.

The lactic acid derivative II used as starting material in the process according to the invention may be readily prepared by reaction of an acid halide of formula X-halide or the corresponding acid anhydride (X—O—X) or a halogenated aldehyde with a derivative of lactic acid of formula IV possessing the S-configuration at carbon atom 2:

(IV)

wherein X and W have the meanings hereinbefore specified. Preferably, the reaction is carried out in the presence of a base, for example an organic base, e.g., pyridine or triethylamine. Generally, reaction takes place at room temperature but, if desired, temperatures in the range −5° C. to +80° C. may be employed. The acid halide or corresponding acid anhydride or halogenated aldehyde may be selected from one of the following:

$V.SO_2.Q$, $V.CO.Q$, $O(CO.Q)_2$ and $H.CO.CV_3$ wherein Q and V have the meaning hereinbefore specified. Preferably an alkylsulphonyl or arylsulphonyl halide is employed, for example methanesulphonyl chloride or paratoluenesulphonyl chloride.

Compound IV is a cheap readily available material where W represents a hydrogen atom, i.e. it is S-(+)-lactic acid. The esters according to formula IV may conveniently be prepared from S-(+)-lactic acid by an esterification reaction with the appropriate alcohol. Alternatively, since S-(—)-ethyl lactate is also a readily available compound this can be converted into the desired lactic acid derivative IV by a transesterification procedure.

It will be appreciated that in the production of compounds of general formula I, wherein W is other than hydrogen, it may according to the circumstances be convenient to introduce the W substituent into the starting material IV or, alternatively, it may be desirable to start with the acid (II; W=H) and introduce the W substituent at a later stage or at the final stage in the process. Equally it may be convenient in the production of compounds of formula I, wherein W is hydrogen to start with an ester and remove the ester grouping at an intermediate or the last stage in the process.

The compounds according to formula I wherein R is a benzoyl group can be prepared by reacting a compound according to formula I, wherein R is a hydrogen atom with a benzoyl halide, such as benzoyl chloride. Suitably, the reaction is carried out in the presence of a solvent such as toluene under reflux conditions. The compounds according to formula I wherein R is a thiobenzoyl group can be prepared by reacting the corresponding benzoyl derivative with a sulphide, such as $P_2S_5$.

Preferably, in the general formula I the alkyl, alkenyl and alkylene groups contain up to 6 carbon atoms, the aryl, aralkyl, and alkaryl groups up to 10 carbon atoms, the halogen unless otherwise specified is chlorine or fluorine and the hetero atoms are oxygen and nitrogen.

The process according to the invention produces two distinct classes of selective herbicides for cereal crops, the first (those of formula I, wherein R is hydrogen) are active against broad-leafed weeds, and the second (those of formula I, wherein R is benzoyl or thiobenzoyl) are active against wild oats. In both classes the preferred compounds are those of formula I, wherein Z is fluorine or chlorine, Y is hydrogen, chlorine or fluorine and W is an alkyl group of up to 6 carbon atoms, e.g., methyl, ethyl or isopropyl.

In order to denote the absolute configuration of the products, starting materials and intermediates used in the process according to the invention the R- and S- notation has been employed as stated in Experientia, Volume 12, pages 81–94, 1956.

The process according to the invention will now be illustrated by the following examples in which the structure of all the compounds synthesized has been confirmed by infrared and NMR techniques:

EXAMPLE

The following compounds were prepared:

| Reaction number | | Compound |
|---|---|---|
| 1 | S-(—)-(lactic acid, methyl ester) | A |
| 3 | S-(—)-(2-mesyloxypropionic acid, methyl ester) | B |
| 5 | R-(+)-(2-(3-chloro-4-fluoroanilino)-propionic acid, methyl ester) | C |
| 6 | R-(—)-(2-(N-benzoyl-3-chloro-4-fluoro-anilino)propionic acid, methyl ester) | D |
| 10 | S-(—)-(2-mesyloxypropionic acid, ethyl ester) | E |
| 21 | S-(—)-(lactic acid, isopropyl ester) | F |
| 23 | S-(—)-(2-mesyloxypropionic acid, isopropyl ester) | G |
| 25 | R-(+)-(2-(3-chloro-4-fluoroanilino)-propionic acid, isopropyl ester) | H |
| 26 | R-(—)-(2-(N-benzoyl-3-chloro-4-fluoro-anilino)propionic acid, isopropyl ester) | I |
| 31 | R-(+)-(2-(3,4-dichloroanilino)propionic acid, ethyl ester) | J |
| 32 | R-(—)-(2-(N-benzoyl-3,4-dichloroanilino)-propionic acid, ethyl ester) | K |
| 38 | R-(+)-(2-(3,4-dichloroanilino)propionic acid, isopropyl ester) | L |
| 39 | R-(—)-(2-(N-benzoyl-3,4-dichloroanilino)-propionic acid, isopropyl ester) | M |

Compounds C, D, H, I, J, K, L and M are the herbicidally active compounds for which the process according to the invention is designed, and Compounds A, B, E, F and G are intermediates for use in the production of the herbicidally active compounds.

Compounds C, H, J and L are dextro-rotatory selective herbicides against broad-leafed weeds in cereal crops whereas Compounds, D, I, K and M are laevo-rotatory selective herbicides against wild oats in cereal crops.

The Compounds A to M were prepared by the methods summarized in the following Table:

TABLE

| Reaction number | Reactants[a] | Moles | Temp. (°C.) | Time (h) | Product compound | Yield (%)[e] | Rotation $([^a]D^{22})^c$ (degrees) | mp or bp[d] |
|---|---|---|---|---|---|---|---|---|
| 1 | S-(+)-lactic acid | 3.0 | reflux | 23 | A | 85 | −8.48[g] | 61° at 35 mm |
|  | methanol[f] | 12.0 | | | | | | |
|  | $H_2SO_4$ | 0.025 | | | | | | |
| 3 | S-(—)-Me lactate | 2.0 | 5° | 2 | B | 66 | −70.2[g] | 94° at 0.08 mm |
|  | mesyl chloride | 2.0 | | | | | | |
|  | pyridine | 2.2 | | | | | | |
| 5 | S-(—)-Me lac mes | 1.0 | 105° | 8.5 | C | 79 | +79.0 | 90° at 0.02 mm (33°–35°) |
|  | CFA | 2.5 | | | | | | |
| 6 | Compound C | 0.02 | reflux | 2 | D | 93 | −19.0 | |
|  | benzoyl chloride | 0.02 | | | | | | |
|  | toluene | 0.10 | | | | | | |
| 10 | S-(—)-Et lactate | 5.0 | 10° | 5 | E | 91 | −65.8[g] | 108° at 0.4 mm |
|  | mesyl chloride | 5.8 | | | | | | |
|  | pyridine | 5.3 | | | | | | |
| 21 | S-(+)-lactic acid | 10.0 | reflux | 36 | F | 71 | −9.8[g] | 78° at 35 mm |
|  | isopropanol | 40.0 | | | | | | |
|  | benzene | 5.0 | | | | | | |
|  | $H_2SO_4$ | 0.12 | | | | | | |

TABLE-continued

| Reaction number | Reactants[a] | Moles | Temp. (°C.) | Time (h) | Product compound | Yield (%)[e] | Rotation ([α]$_D^{22}$)[c] (degrees) | mp or bp[d] |
|---|---|---|---|---|---|---|---|---|
| 23 | S-(−)-Pr$^i$ lac mesyl chloride pyridine | 0.5 0.5 1.0 | 6°–15° | 3 | G | 78 | −59.8[g] | 83° at 0.5 mm |
| 25 | S-(−)-Pr$^i$ lac mes CFA | 3.0 7.5 | 111°–149° | 14 | H | 79 | +87.3 | 36°–38° (66°–67°) |
| 26 | Compound H benzoyl chloride toluene | 2.3 2.4 10.0 | reflux | 4 | I | 96 | −26.6[y] | 69°–71° (59°–61°) |
| 31 | S-(−)-Et lac mes DCA | 3.4 8.8 | 110° | 24 | J | 89 | +86.0 | (38°–41°) |
| 32 | Compound J benzoyl chloride toluene | 2.0 2.1 7.7 | reflux[s] | 2 | K | 93 | −26.1 | 86°–92° |
| 38 | S-(−)-Pr$^i$ lac mes DCA | 2.0 5.0 | 110° | 23 | L | 78 | +100.2 | 65°–67° |
| 39 | Compound L benzoyl chloride toluene | 1.23 1.29 5.0 | reflux | 4 | M | 74 | −31.0 | 51°–53° (172°–174° at 0.3 mm) |

NOTES
[a] lac = lactate; mes = mesylate; CAF = 3-chloro-4-fluoroaniline; DCA = 3,4-dichloroaniline.
[c] Measurements are at C2, methanol.
[hu d] Melting point of corresponding racemate given in brackets, boiling points are the same within experimental error; pressures given in mm of mercury for all boiling points.
[e] Yields are of the purified (distilled or crystallized) products unless otherwise stated. Yields of crude products are higher, these crude materials are probably satisfactory as intermediates.
[f] 150 ml benzene was also used.
[g] Observed neat rotation in a 1 dcm cell, i.e., this value is [a] × the density of the liquid.
[y] Apparent optical purity is 95%.
[s] Reflux is necessary to retain optical activity.

The preferred herbicides, the selective wild oat herbicides for cereal crops were prepared according to the reaction sequences shown in the following Table. The starting material and the overall yield based on the starting material are also given.

| Compound | Starting material | Reaction sequence | Overall yield (%) |
|---|---|---|---|
| D | S-(+)-lactic acid | 1 + 3 + 5 + 6 | 41 |
| I | S-(+)-lactic acid | 21 + 23 + 25 + 26 | 42 |
| K | S-(−)-ethyl lactate | 10 + 31 + 32 | 76 |
| M | S-(+)-lactic acid | 21 + 23 + 38 + 39 | 32 |

We claim:

1. A process for preparing a compound of the formula

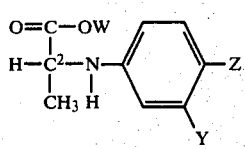

having the R-configuration at carbon atom 2, wherein Y is hydrogen, chlorine or fluorine, Z is chlorine or fluorine, and W is hydrogen or alkyl of from one to six carbon atoms, which consists of treating a compound of the formula

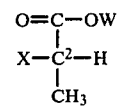

having the S-configuration at carbon atom 2, wherein X is Q—SO$_2$—O—, Q—C(O)— or CV$_3$—CH(OH)—O—, wherein V is chlorine, bromine or fluorine and Q has up to ten carbon atoms and is alkyl, phenyl or alkyl-substituted phenyl, with an aniline of the formula

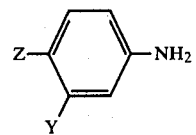

in the presence of a base selected from alkali metal carbonates, alkali metal bicarbonates and an excess of said aniline, at a temperature within the range of 50° C. to 200° C.

2. A process according to claim 1 wherein W is alkyl, X is Q—SO$_2$—O— and Q is methyl or 4-methylphenyl.

3. A process according to claim 2 wherein the base is an alkali metal carbonate or bicarbonate.

4. A process according to claim 3 wherein the base is sodium carbonate and the treatment is conducted at a temperature within the range of from 130° C. to 170° C.